United States Patent [19]

Al-Muddarris

[11] Patent Number: 4,513,162

[45] Date of Patent: Apr. 23, 1985

[54] DEHYDROGENATION PROCESS

[75] Inventor: Ghazi R. Al-Muddarris, Surrey, England

[73] Assignee: Davy McKee Aktiengesellschaft, Frankfurt am Main, Fed. Rep. of Germany

[21] Appl. No.: 568,523

[22] Filed: Jan. 6, 1984

Related U.S. Application Data

[63] Continuation-in-part of Ser. No. 409,090, Aug. 18, 1982, abandoned.

[30] Foreign Application Priority Data

Aug. 18, 1981 [GB] United Kingdom ............... 8125140

[51] Int. Cl.$^3$ .............................................. C07C 5/34
[52] U.S. Cl. .................................... 585/654; 422/202; 422/204; 585/659; 208/132
[58] Field of Search ............... 585/654, 659, 661, 662; 208/132; 422/204, 202

[56] References Cited

U.S. PATENT DOCUMENTS

| | | | |
|---|---|---|---|
| 2,289,922 | 7/1942 | Mickler | 585/659 |
| 3,692,701 | 9/1972 | Box, Jr. | 585/660 |
| 3,719,721 | 3/1973 | Hansford | 585/663 |
| 3,770,812 | 11/1973 | Blood et al. | 585/654 |
| 3,887,495 | 6/1975 | Juguin et al. | 585/654 |
| 4,048,245 | 9/1977 | Pollitrer et al. | 585/660 |
| 4,056,576 | 11/1977 | Gregory et al. | 585/660 |
| 4,108,913 | 8/1978 | Spoerke et al. | 585/663 |
| 4,309,275 | 1/1982 | Mulaskey | 585/654 |
| 4,334,116 | 6/1982 | Valenji et al. | 585/660 |

FOREIGN PATENT DOCUMENTS

| | | | |
|---|---|---|---|
| 232379 | 7/1959 | Australia | 585/654 |
| 632291 | 11/1949 | United Kingdom | 585/654 |
| 837688 | 6/1960 | United Kingdom | 585/654 |
| 946583 | 1/1964 | United Kingdom | 585/654 |
| 1045698 | 10/1966 | United Kingdom | 585/654 |
| 1197537 | 7/1970 | United Kingdom | 585/654 |
| 1238468 | 7/1971 | United Kingdom | 585/654 |
| 1225324 | 3/1972 | United Kingdom | 585/654 |
| 1271457 | 4/1972 | United Kingdom | 585/654 |
| 1290061 | 9/1972 | United Kingdom | 585/654 |
| 1538107 | 1/1979 | United Kingdom | 585/654 |
| 1550873 | 8/1979 | United Kingdom | 585/654 |
| 2039294 | 8/1980 | United Kingdom | 585/654 |

OTHER PUBLICATIONS

Production of Mono- and Diolefins by Catalytic Dehydrogenation of LPG, R. G. Craig et al., Houdry Technology Reports, No. 100.2.
UOP Oleflex Process for LPG-Paraffin Dehydrogenation, B. V. Vora et al., UOP Solutions Through Technology.
Catalytic LPG Dehydrogenation Fits in '80's Outlook, Roy C. Berg et al., Oil & Gas Journal—Nov. 10, 1980.

*Primary Examiner*—Delbert E. Gantz
*Assistant Examiner*—A. Pal
*Attorney, Agent, or Firm*—Bernard, Rothwell & Brown

[57] ABSTRACT

A process and apparatus for dehydrogenating alkanes such as iso-butane comprises contacting the alkane in admixture with steam under dehydrogenation conditions with a dehydrogenation catalyst. The catalyst is substantially free of Group VIII metals of Atomic Number 27 and higher. The catalyst is provided in a heated tubular reactor which preferably contains groups of tubes mounted in a furnace each group of tubes having a common header, to enable continuous dehydrogenation, while permitting catalyst reactivation.

14 Claims, 2 Drawing Figures

DEHYDROGENATION PROCESS

This is a continuation in part of application Ser. No. 409,090 filed Aug. 18, 1982, now abandoned.

FIELD OF THE INVENTION

This invention relates to a process and apparatus for dehydrogenating alkanes.

BACKGROUND OF THE INVENTION

Dehydrogenation of alkanes to unsaturated hydrocarbons, mainly to mono-olefins, is described in the literature and is practised on a commercial scale.

According to one proposal an alkane feed is contacted at sub-atmospheric pressure and at an elevated temperature with a preheated charge of catalyst, such as chromium oxide on alumina, in a fixed bed reactor. For further details of the catalyst reference should be made to U.S. Pat. No. 3,711,569. Due to the endothermic nature of the dehydrogenation reaction the catalyst is rapidly cooled on contact with the alkane feed. Carbon is deposited on the catalyst as the reaction proceeds. In order to provide the necessary heat of reaction it is usual after a short while to switch the alkane feed to another reactor whilst the catalyst of the first mentioned reactor is regenerated by burning off the deposited carbon with hot air. The heat liberated raises the temperature of the catalyst back to the desired level (e.g. about 640° C.), whereupon further alkane feed can be supplied to the reactor. In a typical commercial plant there may be three such reactors, each of which remains on stream in turn for a short period (e.g. of the order of 7 to 10 minutes), before the catalyst has cooled to a temperature, e.g. about 540° C., requiring reheating by burning off the accumulated carbon deposit.

This process has the advantage that little or no isomerisation of the product alkane occurs so that n-butane, for example, may be smoothly converted to a mixture of butene-1 and cis- and trans-butene-2, whilst iso-butane can be converted to iso-butylene without any significant amounts of n-butenes being formed. This means that product recovery is facilitated.

A disadvantage of this process is that it is a cyclic process which is subject to considerable temperature variation in operation. Due to its cyclic nature it is relatively complex to operate and the use of multiple reactors inevitably increases the capital cost. Moreover, since each cycle is very short the plant requires constant supervision and is expensive to operate in terms of labour costs. In addition this process is noted for its low selectively for olefin production and results in production of significant quantities of undesirable by-products. Another major disadvantage is that it is operated under vacuum and so the plant must incorporate not only vacuum equipment but also compression equipment which is required for product recovery.

Another proposal, which has proceeded as far as the pilot plant stage, is described in an article "Catalytic LPG dehydrogenation fits in 80's outlook" by Roy C. Berg et al at page 191 of Oil & Gas Journal for Nov. 10, 1980. According to this proposal a mixture of alkane and hydrogen is contacted with a platinum-containing catalyst in a number of series-connected stacked reactors at a temperature in the range of from about 550° C. to about 600° C. In this design a moving bed of catalyst is used in which catalyst is continuously withdrawn from the bottom of the reactor system and then passed to a regenerator in which it is continuously regenerated to remove carbon deposits and reheat the catalyst before being recycled to the top of the reactor system.

Although this proposal has the advantage of continuous reaction, isomerisation of product alkenes may occur. For example, it is estimated according to Table 4 of the above-mentioned article in Oil & Gas Journal that, in addition to 80 parts by weight of iso-butylene, there will be typically formed per 100 parts by weight of iso-butane feedstock 9 parts by weight of n-butenes. The separation of n- and iso-butenes is relatively difficult and so product recovery is complicated in this process. To maximise yield of iso-butene it is necessary to separate and recover the n-butenes, to hydrogenate these to n-butane, to isomerise this n-butane to iso-butane, and to recycle this to the hydrogenation process. Moreover the platinum-containing catalyst is susceptible to poisoning by impurities in the feedstock. Thus it is necessary to purify the feedstock rigorously in order to remove such impurities or at least to reduce their concentrations to acceptably low levels.

In yet another process (which, it is believed, has also not proceeded past the pilot plant stage) a mixed feed containing alkane and steam is contacted, in the absence of free oxygen, with a Group VIII metal catalyst supported on a highly calcined catalyst support such as alumina, silica or a Group II metal aluminate spinel. For further details regarding this process reference should be made to U.S. Pat. No. 3,641,182 as well as to U.S. Pat. Nos. 3,670,044; 3,692,701; 3,674,706; 4,005,985; 3,761,539; 3,957,688; 3,894,110; 3,880,776; 4,041,099; 4,191,846; 4,169,815; and 4,229,609. In this process a number of fixed tube reactors are used, the alkane feed stream being switched from one reactor to the other whilst the catalyst of the first-mentioned reactor is regenerated, typically by passing a mixture of steam and air through the catalyst.

Although this proposal has the advantage that the catalyst can be used for quite long periods between regenerations, e.g. several hours or so, it still suffers from the drawback of being a cyclic process and requires high capital investment.

There is accordingly a need to provide a continuous process for dehydrogenation of alkanes in which yields of product olefin are maximized with essentially no co-isomerisation to other olefins.

OBJECTS OF THE INVENTION

It is an object of the present invention to provide a process for dehydrogenating alkanes which causes minimal isomerisation of product olefin or olefins.

It is a further object of the present invention to provide a process for dehydrogenating alkanes which can be operated on an essentially continuous basis and wherein catalyst reactivation can be carried out without the need for complete shutdown.

It is a further object of the invention to provide a reactor for use in the dehydrogenation of alkanes which allows catalyst reactivation to be carried out while continuing to operate the process.

SUMMARY OF THE INVENTION

According to the present invention there is provided a continuous process annd tubular reactor for dehydrogenating an alkane wherein a plurality of groups of caatalyst filled tubes mounted in a furnace are utilized to catalytically contact the alkane in an admixture with steam under dehydrogenating conditions. Alkane flow to the corresponding groups of tubes through respective headers for the groups of tubes is sequentially and cyclically turned on and off together with admitting a reactivating medium in order to periodically reactivate the catalyst without interruption of the furnace operation.

DESCRIPTION OF THE PREFERRED EMBODIMENTS

The process of the invention is applicable to essentially any dehydrogenatable alkane or mixture of dehydrogenatable alkanes. Preferably the alkane or alkanes contains or contain from 2 to about 20 carbon atoms, more preferably from 2 to about 10 carbon atoms. Such alkanes may be selected from straight chain hydrocarbons and branched chain hydrocarbons. Typical alkanes include ethane, propane, n-butane, iso-butane, n-pentane, iso-pentane, and the like.

An important feature of the invention is the use of an externally heated tubular reactor. Preferably the reactor comprises a multi-tubular reactor comprising a plurality of tubes suitably mounted in a furnace. Such a furnace may be of any suitable design. For example, the furnace may be of the side-fired or of the top-fired type. By providing a multiplicity of tubes, arranged in groups, conveniently in rows, it is readily possible to operate the process continuously, even while reactivating the catalyst in a number of the tubes, which it will periodically be necessary to do. If the tubes are arranged in rows in the furnace, then it can readily be arranged that each row is supplied through a common header so that the supply of reactants to the tubes of a given row can be controlled by a valve in that header. The ratio of the number of groups of tubes operating under dehydrogenating conditions to the number of groups of tubes undergoing reactivation is determined by the rate of catalyst deactivation.

The alkane is supplied in admixture with steam. Optionally hydrogen may be included in the mixture which is contacted with the catalyst. Typically alkane:-steam ratios range from about 1:1 to about 1:25 by volume or more. Usually, however, the alkane:steam ratio will lie in the range of from about 1:2 to about 1:20 by volume. When hydrogen is present this may be in a ratio of alkane:hydrogen in the range of from about 1:2 to about 10:1 by volume.

Typical dehydrogenation conditions include the use of elevated total pressures in the range of from about 2 to about 25 ata, preferably in the range of from about 3 to about 20 ata, as well as temperatures in the range of from about 450° C. to about 700° C. Typically the reaction temperature lies in the range of from about 500° C. to about 650° C. Preferably the process is conducted so that the space velocity of the reactant stream (i.e. hydrocarbon plus steam plus any hydrogen present) lies in the range of from about 1 to about 10 kg/hr/liter of catalyst.

As catalyst there is in one embodiment preferably used a dehydrogenation catalyst which is substantially free from Group VIII metals as defined above. Generally speaking this means that the catalyst is prepared from starting materials that are normally free from Group VIII metals of Atomic Number 27 and higher, such as nickel, platinum, palladium, ruthenium, iridium, rhodium, and osmium. The catalyst must also be substantially free from metals that promote steam reforming reactions, e.g. potassium. Amongst catalysts that can be considered for use in the present invention there may be mentioned in particular solid refractory catalysts, such as zirconia, chromiumoxide-promoted iron oxide, alumina, magnesite, silica-based refractories (which are substantially free from quartz), spinels, more particularly materials of the formula $MO.R_2O_3$ in which M is a bivalent metal ion such as a magnesium or ferrous ion, and R is an aluminum, chromium or ferric ion, and the like. Preferably the selected catalyst should have a high surface area:volume ratio. Usually it will be preferred, before use, to calcine the catalyst at high temperatures, typically about 1000° C. to about 1400° C., for extended periods, e.g. up to about 100 hours.

Prior to contact with the catalyst it will usually be desirable to desulphurise the alkane feedstock. Any of the known methods of desulphurising alkanes can be used.

The process may be operated continuously. Reactivation of the catalyst in some of the tubes can be carried out during operation of the process in the other tubes by shutting off the alkane feed to the selected tubes, whilst maintaining the supply of steam to them, and admixing air with the steam in an amount sufficient to provide an oxygen content typically from about 0.1 to about 2% by volume of oxygen in order to burn off deposited carbon and any polymeric by-products. After a suitable period of reactivation the supply of air is then shut off and alkane again admitted to the relevant tubes or rows of tubes.

The dehydrogenation reaction is endothermic, as already mentioned. It is accordingly desirable to ensure that the volume of catalyst in each tube, and the length of heated catalyst-filled tube, are sufficient to enable the yield of olefin per pass to be maximised. Usually the conversion per passwill be less than 100%, typically about 30% to about 60%, so that after product recovery unreacted alkane is preferably recycled to the process for further reaction on a subsequent pass.

When operating the process under elevated pressure, product recovery is facilitated since steam can be condensed at temperatures well above the boiling points of the alkanes and of the olefin products. Subsequent product recovery steps may include, for example, refrigeration, adsorption, or absorption in oil, or compression and cooling, or a combination of two or more such techniques.

In the process of the invention dehydrogenation is effected under controlled temperature conditions, using a catalyst that has high selectivity to the desired olefin product, whilst a relatively long residence time is provided in the or each catalyst filled tube due to the large external surface area of the tube that is required for heat transfer and due to the high surface area:volume ratio of the catalyst. Hence the reaction proceeds substantially to equilibrium and so dehydrogenation is governed by the approach to thermodynamic equilibrium and is not controlled by the kinetics of the dehydrogenation reaction.

Since the process of the invention substantially avoids the use of Group VIII metal catalyst of Atomic Number 27 or higher which tend to isomerise olefins, the product olefin can be recovered readily from the reaction product mixture since it is not formed in admixture with a significant amount of isomeric olefins. Moreover by diluting the alkane feed with steam the corresponding partial pressure of alkane is reduced, hence increasing the conversion to olefins, whilst retaining the advantages of supra-atmospheric pressure operation such as ready separation of hydrocarbons (i.e. alkanes plus olefins) from the diluent. In addition the process of the invention can be operated continuously for extended periods, and the use of a single furnace represents a significant capital cost saving besides enabling ready catalyst reactivation.

In order that the invention may be clearly understood and readily carried into effect a preferred form of plant operating according to the process of the invention will now be described, by way of example only, with reference to the accompanying drawings wherein:

It will be appreciated by those skilled in the art that, since the drawings are diagrammatic only, many items of equipment which would be needed in a commercial plant for successful operation, have been omitted for the sake of simplicity. Such items of equipment, for example, temperature gauges, pressure gauges, pumps, valves, pressure controllers, etc., will be provided in accordance with standard chemical engineering practice and form no part of the present invention.

Figure 1:
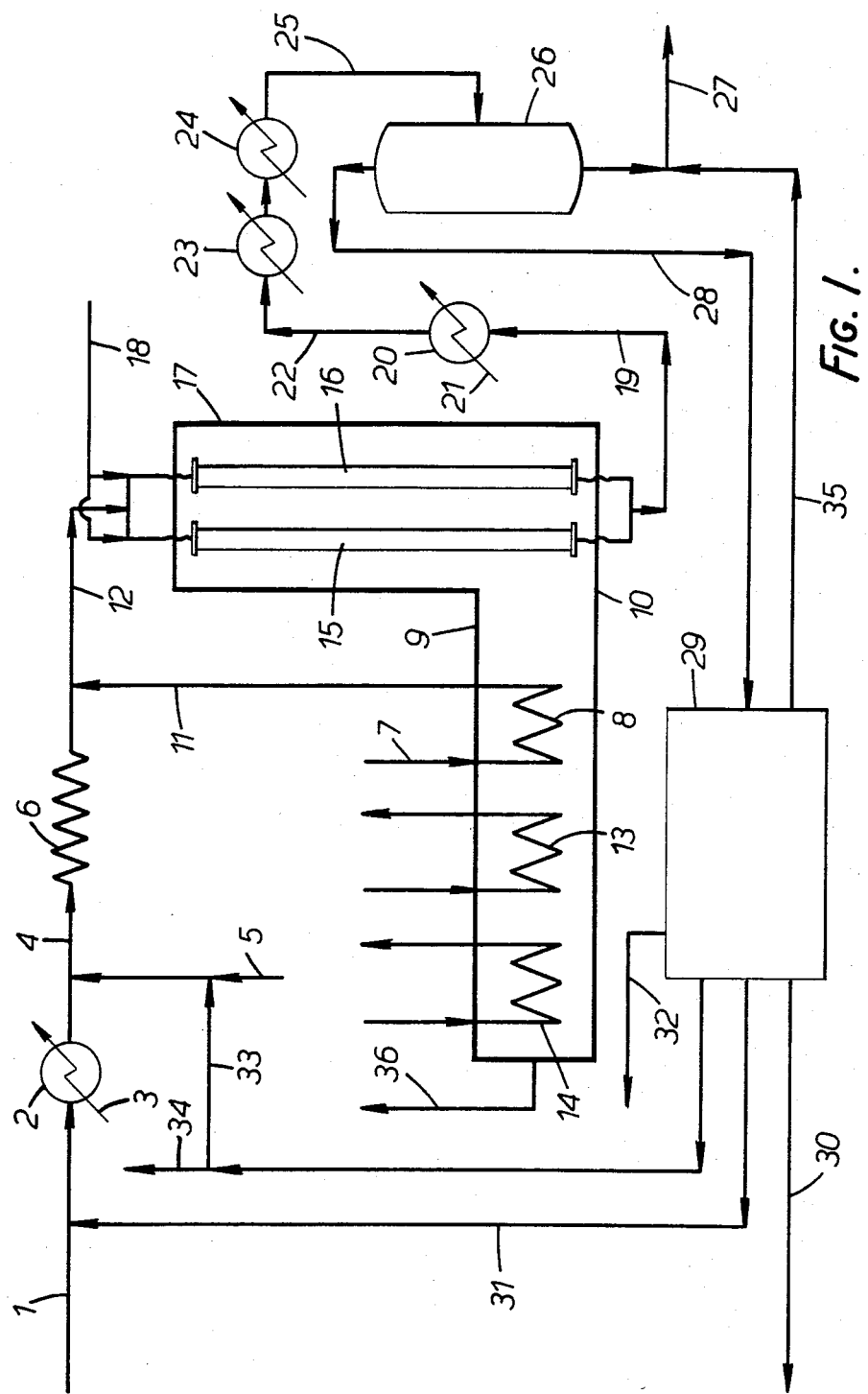
FIG. 1 is a flow sheet of an iso-butane dehydrogenation plant.

Referring to FIG. 1 of the drawings a liquid desulphurised iso-butane feed is supplied via line 1 to a vaporiser 2 which is supplied with a suitable heating medium, e.g,. steam, by way of line 3.

The resulting gaseous iso-butane in line 4 is admixed with hydrogen supplied by way of line 5 in a ratio of 1:1 by volume annd the gaseous mixture formed passes on to a preheater 6.

Steam is supplied from a steam drum (not shown) by way of line 7 to a superheater 8 which is mounted in the heat recovery section 9 of a furnace 10 or steam may alternatively be supplied by a separate preheating furnace. The superheated steam passes from superheater 8 in line 11 and is mixed with the preheated iso-butane/hydrogen mixture from preheater 6 and passes on in line 12.

Although preheater 6 is shown as being separately fired it could equally be mounted in heat recovery section 9. Also mounted in heat recovery section 9 are a waste heat boiler 13 for raising steam and an air preheater 14 for preheating combustion air for the furnace 10.

The preheated mixture in line 12 comprises an iso-butane/hydrogen/steam mixture in a ratio of 1:1:6 by volume at a pressure of about 6.5 ata. It is then passed by way of suitable valves (not shown) and headers (not shown) to a multiplicity of catalyst-filled tubes 15, 16 mounted in the fired section 17 of the furnace 10. The space velocity in the tubes 15, 16 is in the range of from about 1 to about 10 kg/hr/liter of catalyst. The fired section 17 is heated by means of a plurality of burners (not shown) which can be mounted, as desired, either in the arch of the furnace (as in a top-fired furnace) or in the side walls thereof (as in a side-fired furnace) for contacting the tubes with heating medium, i.e. heated gases, radiant energy etc. Suitable arrangements are made to supply such burners with fuel, e.g. natural gas or fuel oil, and with hot combustion air from preheater 14 in the usual way.

It will be appreciated that, for the sake of simplicity, only two rows 15, 16 of catalyst-filled tubes are shown in the drawing. In practice, however, at least three rows of tubes will be provided, for example 12 rows of 20 tubes each. Each row of tubes 15, 16 is conveniently connected to a common header, flow through which is controlled by a suitable valve (not shown). Hence when catalyst reactivation is required it is a simple matter to shut off one or more rows of tubes in turn and to reactivate the catalyst by admitting to the relevant row or rows of tubes a mixture of steam and air, suplied by way of lines 18, having an oxygen content of from about 0.1 to about 2% by volume.

Figure 2:
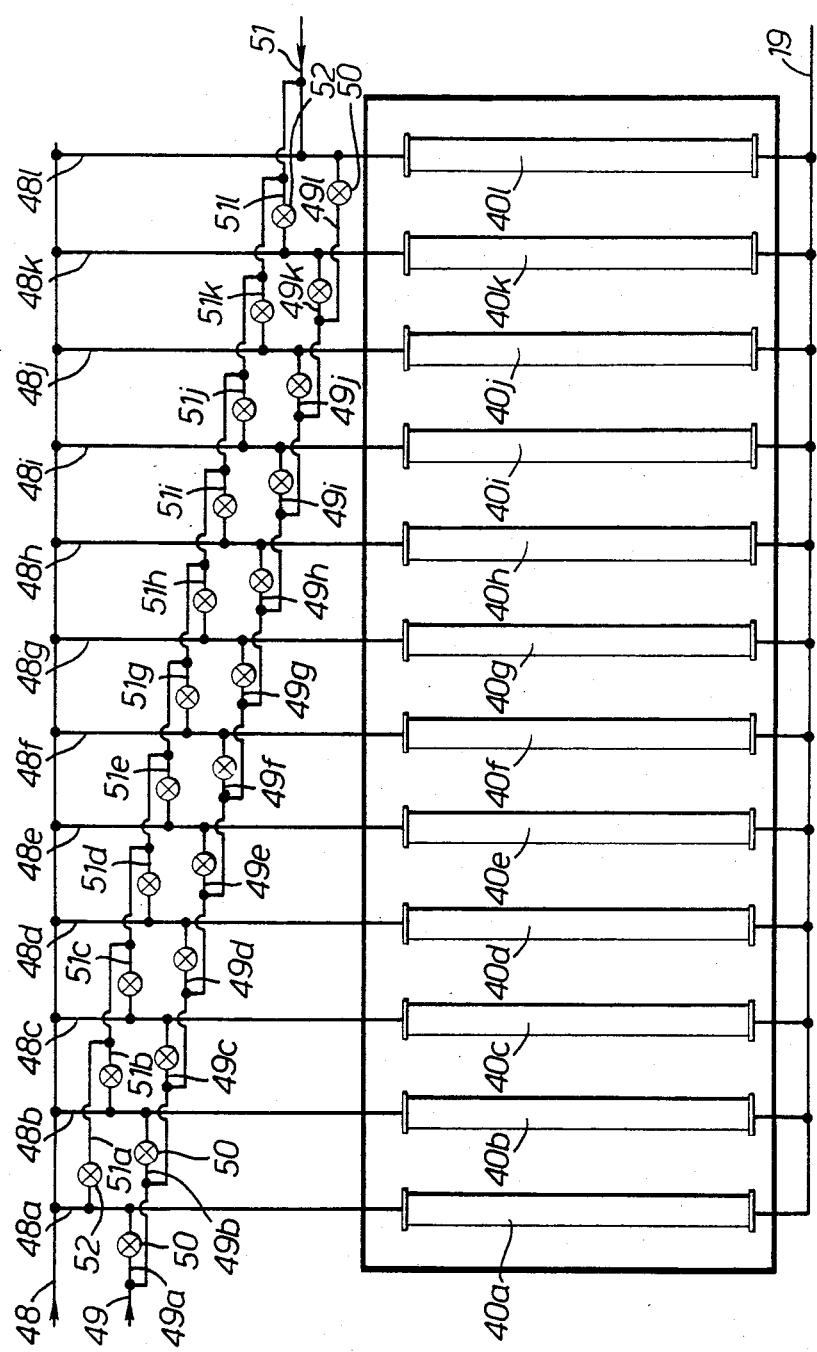
FIG. 2 shows a modified arrangement of part of the dehydrogenation plant.

In the modified arrangement shown in FIG. 2, the iso-butane and steam are supplied on independent lines to twelve rows 40a to 40l, each having twenty catalyst-filled tubes. Thus steam is supplied on line 48, which branches into lines 48a to 48l to supply rows of tubes 40a to 48l respectively. Iso-butane is supplied on line 49 which branches into lines 49a to 40l respectively, a valve 50 being arranged in each branch 49a to 49l to shut off the iso-butane supply to one or more rows of tubes as desired. Air is supplied on line 51, which likewise branches into lines 51a to 51l to supply each row of tubes 40a to 40l respectively, a valve 52 being arranged in each branch to control air supply to the tubes as desired. Thus for reactivation of one or more rows of catalyst-filled tubes, it is only necessary to shut off the iso-butane feed stream to those tubes while maintaining the steam supply and add the appropriate amount of air to the steam. The remaining tubes not requiring regeneration are unaffected. The effluent from all the tubes, from both dehydrogenation and reactivation, can be drawn off as a common stream on line 19. It will be understood that for example, each group of tubes 40a to 40l may operate for say 11 hours with regeneration for one hour. Thus at any one time eleven groups of tubes are dehydrogenating while one group is regenerating. This leads to a high efficiency of operation. Further by combining effluent from all the tubes in a common effluent stream on line 19, the yield and composition of the effluent in the stream of line 19 is kept as constant as possible, since the catalyst in each group of tubes will be at a different stage of activation while the average product composition is relatively constant. Moreover, as a small number for example two groups only out of the twelve groups of tubes are involved in line changing at any one time, i.e., one group being taken "off line" for regeneration while the newly regenerated group is brought back "on line", any consequent pressure fluctuation is minimized and any need to provide empty vessels to absorb such pressure fluctuations is reduced.

In the arrangement shown in both FIGS. 1 and 2 the hot reaction mixture exits the lower ends of the vertically arranged catalyst tubes 15, 16 or 40a to 40l at a temperature of 570° C. and is passed by way of line 19 to a boiler 20 which is fed with boiler feed water in line 21. The somewhat cooled mixture passes on in line 22 to heat recovery section 23 (e.g. a reboiler for a distillation column) and then to cooling stage 24. The mixture exiting cooling stage 24 comprises gaseous hydrocarbons and water which passes via line 25 to separator 26. The condensed water is recovered in line 27 and can be recycled for use as boiler feed water or cooling water.

A mixture of hydrogen and hydrocarbon gases exits the top of separator 26 in line 28. This is passed to product recovery zone 29 in which iso-butylene is separated both from unreacted iso-butane and also from any lighter hydrocarbons present and from hydrogen. Product iso-butylene is passed by way of line 30 to storage or is exported beyond battery limits for production of, for example, alkylate petroleum or methyl t-butyl ether.

Unreacted iso-butane is recycled to line 1 by way of line 31. A hydrocarbon purge stream is taken in line 32. Hydrogen is recycled to the process by way of line 33, a purge stream being taken by way of line 34. Further water is separated in product recovery zone 29 and is recovered in line 35.

Reference numeral 36 indicates the combustion products pathway from furnace 10 to the furnace stack (not shown).

Product recovery section 29 is designed in conventional manner and may incorporate provision for refrigeration, compression, turbo-expansion, oil absorption or adsorption, and similar techniques, or a combination of two or more thereof.

In operation of the illustrated plant the process can be run essentially continuously using a single furnace, individual rows of tubes being taken out of service at relatively infrequent intervals as required to reactivate the catalyst. The use of a single furnace greatly simplifies the operating procedures and hence enable a reduction in the capital investment costs of the plant.

In the illustrated plant make up hydrogen is supplied in line 5. Such hydrogen is, however, optional.

What is claimed is:

1. A continuous process for dehydrogenating an alkane comprising:
    providing an admixture of said alkane with steam
    contacting a plurality of at least three groups of dehydrogenation catalyst containing tubes with a heating medium within a single furnace chamber of a fired reactor;
    feeding the admixture to common headers for each group of the catalyst containing tubes;
    contacting the admixture with the catalyst in the groups of tubes in the fired tubular reactor under endothermic dehydrogenating conditions;
    cyclically shutting off in turn a minority of the groups of tubes from alkane flow for reactivation, the ratio of the number of groups of tubes operating under dehydrogenating conditions to the number of groups of tubes undergoing reactivation having been determined as a function of the rate of catalyst deactivation;
    admitting a reactivating medium to said minority of groups of tubes to cause exothermic reactivation of the catalyst, whereby the ctalyst in each minority of groups of tubes is cyclically reactivated during the process; and
    admixing the effluents from all the tubes, including both tubes operating under dehydrogenating conditions and tubes operating under reactivation conditions, to form a common effluent stream.

2. The process of claim 1 comprising controlling the dehydrogenating conditions so that the reaction proceeds substantially to equilibrium, whereby dehydrogenation is governed by the approach to thermodynamic equilibrium rather than by the kinetics of the dehydrogenation process.

3. The process of claim 2 comprising controlling dehydrogenating conditions selected from temperature, catalyst type, selectivity and residence time in the catalyst tubes.

4. The process of claim 2 comprising controlling the dehydrogenating conditions to give a conversion per pass of from about 30% to about 60%.

5. The process of claim 1, wherein the reactivating medium is a mixture of air and steam.

6. The process of claim 5, comprising;
    shutting off one or more groups of tubes from alkane flow while maintaining the steam supply; and
    admixing air with the steam in an amount sufficient to provide an oxygen content sufficient to burn off deposited carbon in the tubes.

7. The process of claim 1, wherein the alkane to be dehydrogenated comprises an alkane or mixture of alkanes containing from 2 to 20 carbon atoms.

8. The process of claim 7, wherein the alkane is iso-butane.

9. The process of claim 1, comprising supplying the alkane and steam to the reactor in a ratio of from about 1:1 to about 1:25 by volume.

10. The process of claim 1 comprising admixing hydrogen with the alkane and steam.

11. The process of claim 10 comprising admixing hydrogen in a ratio of alkane to hydrogen of about 1:2 to about 10:1 by volume.

12. The process of claim 1 comprising carrying out the dehydrogenation at an elevated pressure of about 2 to about 25 atmospheres.

13. The process of claim 1 comprising contacting the admixture and catalyst at a reaction temperature lying in the range of from about 500 degrees C. to about 650 degrees C.

14. The process of claim 1 comprising passing the admixture through the reactor at a space velocity lying in the range of from about 1 to about 10 kg/hr/liter of catalyst.

* * * * *